US006444200B2

(12) United States Patent
Foldvari et al.

(10) Patent No.: US 6,444,200 B2
(45) Date of Patent: *Sep. 3, 2002

(54) COMPOSITION AND METHOD FOR DERMAL AND TRANSDERMAL ADMINISTRATION OF A CYTOKINE

(75) Inventors: Marianna Foldvari, Saskatoon; Sam Kwadwo Attah-Poku, Saskatchewan, both of (CA)

(73) Assignee: PharmaDerm Laboratories, Ltd. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/730,464

(22) Filed: Dec. 4, 2000

Related U.S. Application Data

(63) Continuation of application No. 09/216,500, filed on Dec. 18, 1998, now Pat. No. 6,165,458.
(60) Provisional application No. 60/068,873, filed on Dec. 26, 1997.

(51) Int. Cl.$^7$ .......................... A61K 38/19; A61K 38/20; A61K 38/21; C07K 1/113; C07K 14/52
(52) U.S. Cl. ................ 424/85.1; 424/85.2; 424/85.4; 424/85.5; 424/85.6; 424/85.7; 424/283.1; 530/351; 530/410
(58) Field of Search .................. 530/351, 410; 424/85.1, 85.2, 85.4, 85.5, 85.6, 85.7, 278.1, 280.1, 283.1

(56) References Cited

U.S. PATENT DOCUMENTS 6,165,458 A * 12/2000 Foldvari et al. ............ 424/85.1

FOREIGN PATENT DOCUMENTS

WO 93-12142 * 6/1993

OTHER PUBLICATIONS

Bakouche et al. Acylation of Cell–Associated IL–1 . . . J. Immunology, vol. 147, No. 7, pp. 2164–2169, Oct. 1, 1991.*
Foldvari et al. Palmitoyl derivatives of interferon alpha . . . J. Pharm. Sci. vol. 87, No. 10, pp. 1203–1208, Oct. 1998.*

* cited by examiner

Primary Examiner—Jeffrey E. Russel
(74) Attorney, Agent, or Firm—Judy M. Mohr; Jacqueline F. Mahoney; Perkins Coie LLP

(57) ABSTRACT

A composition for transdermal administration of a cytokine is described. The composition includes a conjugate composed of a cytokine, such as an interferon, and at least one fatty acid moiety covalently attached to the cytokine. The conjugate has enhanced cutaneous delivery relative to the cytokine alone.

5 Claims, 8 Drawing Sheets

Figure 1:
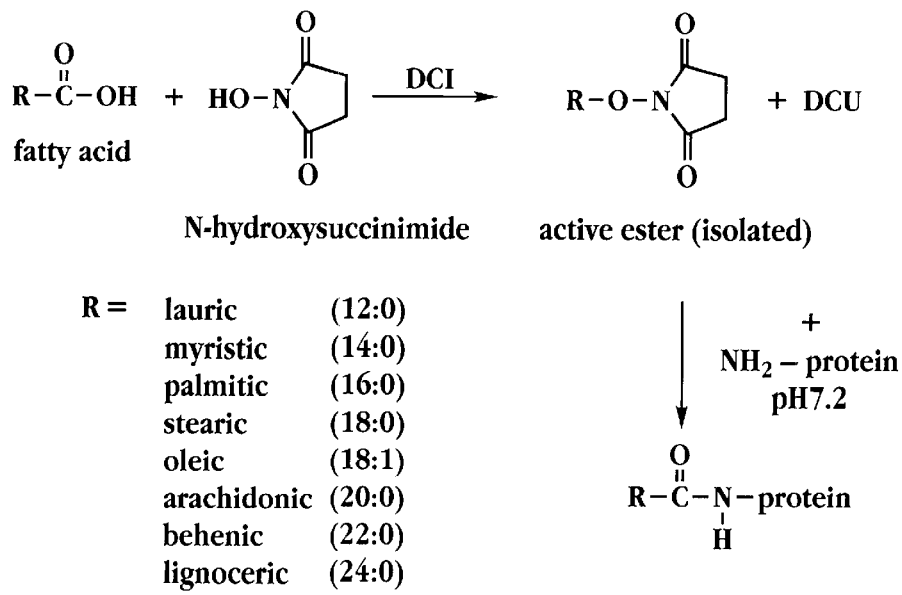

| | |
|---|---|
| CYS ASP LEU PRO GLN THR HIS SER LEU GLY SER | 11 |
| ARG ARG THR LEU MET LEU LEU ALA GLN MET ARG | 22 |
| ARG ILE SER LEU PHE SER CYS LEU LYS ASP ARG | 33 |
| HIS ASP PHE GLY PHE PRO GLN GLU GLU PHE GLY | 44 |
| ASN GLN PHE GLN LYS ALA GLU THR ILE PRO VAL | 55 |
| LEU HIS GLU MET ILE GLN GLN ILE PHE ASN LEU | 66 |
| PHE SER THR LYS ASP SER SER ALA ALA TRP ASP | 77 |
| GLU THR LEU LEU ASP LYS PHE TYR THR GLU LEU | 88 |
| TYR GLN GLN LEU ASN ASP LEU GLU ALA CYS VAL | 99 |
| ILE GLN GLY VAL GLY VAL THR GLU THR PRO LEU | 110 |
| MET LYS GLU ASP SER ILE LEU ALA VAL ARG LYS | 121 |
| TYR PHE GLN ARG ILE THR LEU TYR LEU LYS GLU | 132 |
| ASP LYS TYR SER PRO CYS ALA TRP GLU VAL VAL | 143 |
| ARG ALA GLU ILE MET ARG SER PHE SER LEU SER | 154 |
| THR ASN LEU GLN GLU SER LEU ARG SER LYS GLU | 165 |

Fig. 3

COMPOSITION AND METHOD FOR DERMAL AND TRANSDERMAL ADMINISTRATION OF A CYTOKINE

This application is a continuation of U.S. Application No. 09/216,500 filed Dec. 18, 1998, now U.S. Pat. No. 6,165,458, which claims the benefit of U.S. Provisional Application Ser. No. 60/068,873, filed Dec. 26, 1997, both of which are incorporated herein by reference in their entirety.

FIELD OF THE INVENTION

The present invention relates to a composition for transdermal administration of a cytokine. The composition includes a conjugate composed of a cytokine and at least one fatty acid moiety covalently attached to the cytokine.

BACKGROUND OF THE INVENTION

The routine administration of therapeutic proteins and peptides is hindered by the lack of a reliable and convenient mode of delivery. The oral route is often impractical due to the digestion of proteins in the gastrointestinal tract. Parenteral administration is an alternative, although frequent injections are required due to the short half-life of peptides and this can decrease patient compliance.

Other potential routes of administration for proteins include nasal, pulmonary, rectal, vaginal, ocular and transdermal. The transdermal route offers some advantages in that the skin has low proteolytic activity, so that metabolism of the protein during transit through the skin is minimized thereby improving bioavailability.

One problem with transdermal administration of proteins and peptides is that they may exhibit very low permeability through the skin due to their hydrophilicity and high molecular weight. One approach to overcoming the low skin permeability is directed to temporarily compromising the integrity or physicochemical characteristics of the skin to enhance skin penetration, e.g., using a skin penetration enhancer, employing ultrasonic vibration, removing the epithelial layer by suction or employing an electric current (iontophoresis). These approaches have demonstrated the feasibility of transdermal administration of proteins and peptides, however are associated with skin irritation and/or other disadvantages.

SUMMARY OF THE INVENTION

Accordingly, it is an object of the invention to provide a composition for administration of a protein or peptide transdermally. More specifically, it is an object of the invention to provide a composition for transdermal administration of a cytokine.

In one aspect, the invention includes a pharmaceutical composition for dermal or transdermal administration of a cytokine. The composition includes a conjugate composed of a cytokine and at least one fatty acid moiety having between 12–24 carbon atoms covalently attached to the cytokine. The conjugate has a substantially higher rate of skin penetration than the cytokine alone.

In one embodiment, the cytokine is an interferon or an interleukin, and in a preferred embodiment, the cytokine is interferon α, interferon β, interferon γ, interleukin 1, interleukin 2 or interleukin 13.

The fatty acid to which the cytokine is attached is a saturated fatty acid having between 12–24 carbon atoms or an unsaturated fatty acid having between 12–20 carbon atoms. In preferred embodiments of the invention, the fatty acid is palmitic acid, behenic acid or lignoceric acid.

One preferred conjugate includes interferon α as the cytokine and palmitic acid as the fatty acid.

In another aspect, the invention includes a method for dermal or transdermal administration of a cytokine. The method includes preparing a conjugate, as described above, and applying the conjugate to the skin of a subject in a pharmaceutically acceptable preparation.

In another aspect, the invention includes a method of treating an infection caused by human papilloma virus in a subject by administering topically at the site of infection, a conjugate as described above. In one embodiment of the method, the infection to be treated is genital warts and the cytokine in the conjugate is interferon α.

In another aspect, the invention includes a method of enhancing an immune response to a vaccine, by administrating topically to a patient receiving a vaccine, a conjugate composed of a cytokine and, covalently attached to the cytokine, at least one fatty acid moiety having between 12–24 carbon atoms.

These and other objects and features of the invention will be more fully appreciated when the following detailed description of the invention is read in conjunction with the accompanying drawings.

BRIEF DESCRIPTION OF THE DRAWINGS

FIG. 1 shows a synthetic reaction scheme for acylation of a cytokine;

FIG. 2 shows a synthetic reaction scheme for acylation of interferon with palmitic acid;

FIG. 3 shows the amino acid sequence of interferon α2b (SEQ ID No. 1).

FIGS. 4A–4B are capillary electrophoresis electropherograms showing the time dependence of derivatization of interferon γ with palmitic acid (FIG. 4A) and the effect of protein:reagent ratio on the derivatization (FIG. 4B);

FIGS. 5A–5B are plots of mobility, determined by capillary electrophoresis, as a function of cytokine:fatty acid ester ratio (FIG. 5A) and time (FIG. 5B) for interferon α2b derivatized with palmitic acid (FIG. 5A) and oleic acid (FIG. 5B, closed triangles);

FIG. 6A is a chromatographic profile of palmitoylated interferon α2b on Sephadex G-25:

FIG. 6B is a SDS-PAGE pattern of the corresponding chromatographed fractions of FIG. 6A after silver staining;

FIG. 6C is a SDS-page profile of palmitoylated interferon α2b synthesized under various conditions;

FIGS. 7A–7B are plots showing binding to human keratinocytes of interferon α2a as a function of concentration of interferon α2a (FIG. 7A) and of interferon α2a derivatized with behenic acid (closed circles) and lauric acid (closed diamonds) and interferon α2a treated with DMSO (closed squares) (FIG. 7B);

FIG. 8A is a plot showing in vitro percutaneous absorption through human skin as a function of time of conjugates of interferon α2b and palmitic acid (closed diamonds), oleic acid (open triangles), myristic acid (open diamonds), stearic acid (open circles) and lauric acid (open squares) and of liposomally-entrapped interferon α2b (closed circles) and interferon α2b alone (closed squares); and FIG. 8B is a bar graph showing in vitro cutaneous absorption into human skin after 24 hours of the formulations shown in FIG. 8A, where absorption into whole skin and into skin after removal of the stratum corneum is reported for each formulation.

DETAILED DESCRIPTION OF THE INVENTION

I. Preparation of the Conjugate

As discussed above, the conjugate of the invention is composed of a cytokine and a fatty acid moiety covalently attached to the cytokine. As used herein, a cytokine includes any immune system protein that is a biological response modifier. Generally, cytokines coordinate antibody and T cell immune system interactions and amplify immune reactivity and include monokines synthesized by macrophages and lymphokines produced by activated T lymphocytes and natural killer cells. Monokines include interleukin 1, tumor necrosis factor, α and β interferons and colony-stimulating factors. Lymphokines include interleukins, interferon γ, granulocyte macrophage colony-stimulating factor and lymphotoxin. Cytokines are also synthesized by endothelial cells and fibroblasts.

FIG. 1 shows a synthetic reaction scheme for derivatizing a protein, in particular a cytokine, having amino positions available for covalent attachment, with a fatty acid. In the first step of the process, the N-hydroxysuccinimide ester of the fatty acid is prepared by mixing the fatty acid with N-hydroxysuccinimide in a suitable solvent in the presence of dicyclohexylcarbodiimide. The fatty acid ester is then isolated by recrystallization or other technique. In the second step, the fatty acid ester is mixed with the protein to react with available amino groups to yield the fatty acid linked to the protein through an amide bond.

It will be appreciated that other reaction schemes are suitable to derivatize a protein with a fatty acid. For example, the amide bond formation can be done more selectively by blocking and de-blocking certain groups on the protein. The protein can also be derivatized with the fatty acid through formation of an ester bond.

In studies performed in support of the invention, interferon α, more specifically, interferon α2b, interferon α2a and interferon γ, were derivatized with various fatty acids according to the scheme set forth in FIG. 1. The procedure is suitable for derivatization of other proteins, such as IL-4, IL-12 and GM-CSF.

Figure 2:
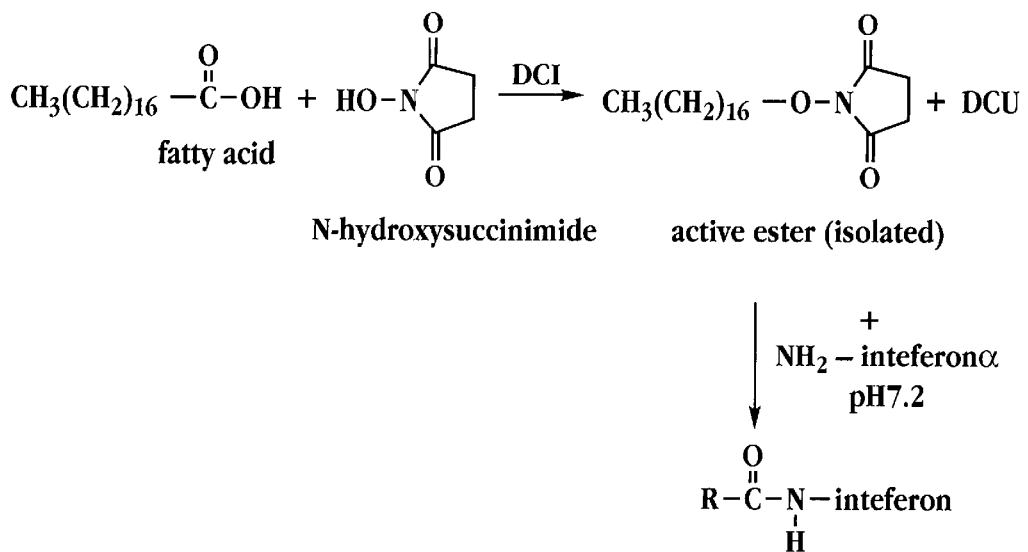

A reaction scheme for fatty acylation of interferon with palmitic acid is illustrated in FIG. 2. Fatty acylation of interferon α by this reaction forms an amide bond which is stable for dosage form development and in biological environments. As described in Example, 1, the first step in the synthesis is to prepare N-hydroxysuccinimide-palmitate, which, in the second step of the process, is reacted with interferon in a suitable solvent, such as dimethylsulfoxide or dimethylformamide.

Interferon α2b is a hydrophilic protein with nine lysine amino acids, which, with reference to FIG. 3, are at positions 31, 49, 70, 83, 112, 121, 131, 134 and 164. These lysine amino acids, in addition to the amino terminal, are available for potential covalent attachment of fatty acids. Interferon α2b has disulfide bonds between residues 1 and 19 and between residues 29 and 138 (Wetzel, *Nature,* 289:606, 1981), and only the latter disulfide bond is critical for maximal antiviral activity (Morehead, et al., *Biochemistry,* 23:2500, 1984). Three structurally distinct domains are important for activity: 10–35, 78–107 and 123–166 (Fish, et al., *J. Interferon Res.,* 9:97, 1989).

As noted above, interferon α has nine lysine residues, as well as the terminal cysteine, for potential acylation. Depending on the availability of these positions for acylation and on the reaction conditions, one or more positions can be derivatized with a fatty acid. The three dimensional structure of interferon α has been constructed by computer modeling for the primary amino acid sequence of consensus interferon α (Korn, et al., *J. Interferon Res.,* 14:1, 1994). The model indicates that the conformationally accessible regions for derivatization within interferon α are domains 29–35, 79–95 and 123–140. Thus, at least the four lysine residues within these regions (positions 31, 83, 131 and 134), plus the terminal amino acid, are conformationally available to bind with a fatty acid.

Because the reaction shown in FIG. 2 is a non-specific acylation synthesis, it is expected that some of the lysine ϵ-amino groups and the terminal amino group on the protein will be acylated. The actual fatty acid-derivatized interferon is likely a mixture containing interferon α acylated to various degrees, i.e., mono-palmitate, di-palmitate, etc. For the purpose of the studies reported herein, the different fractions were not separated or purified. However, it will be appreciated that the fractions can be separated if desired in order to optimize activity and rate of transdermal penetration of the conjugate.

Figure 4A:
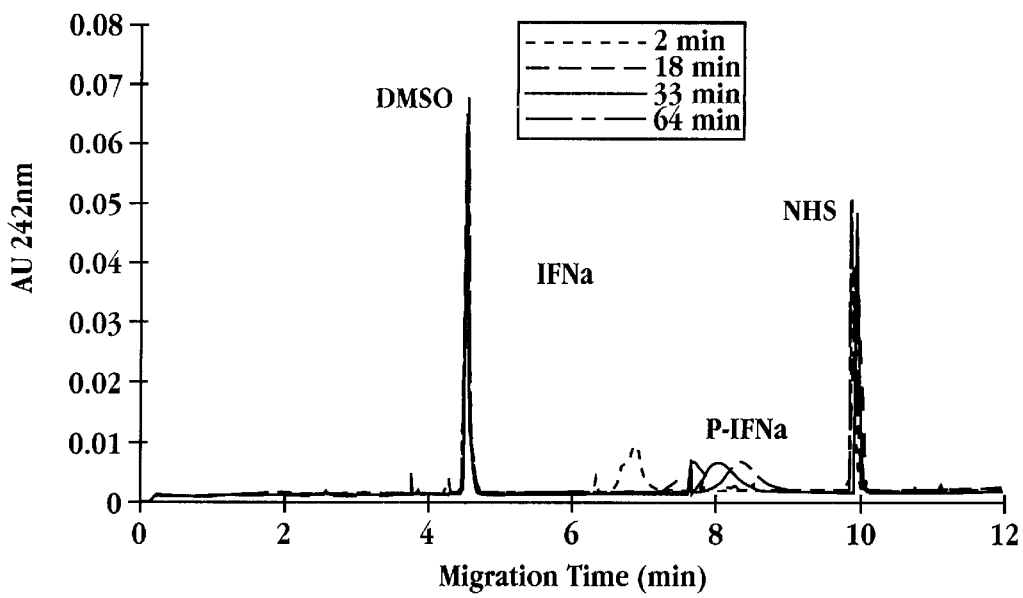
Figure 4B:
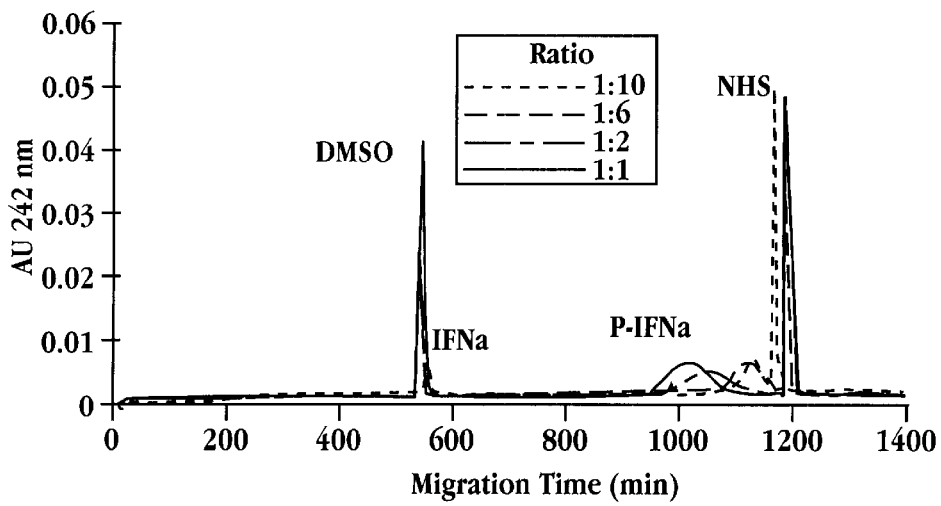
Figure 5A:
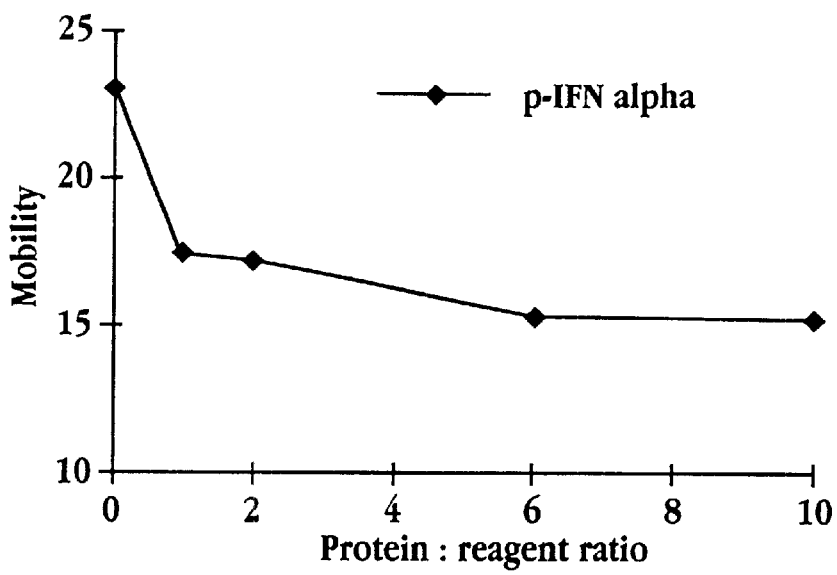
Figure 5B:
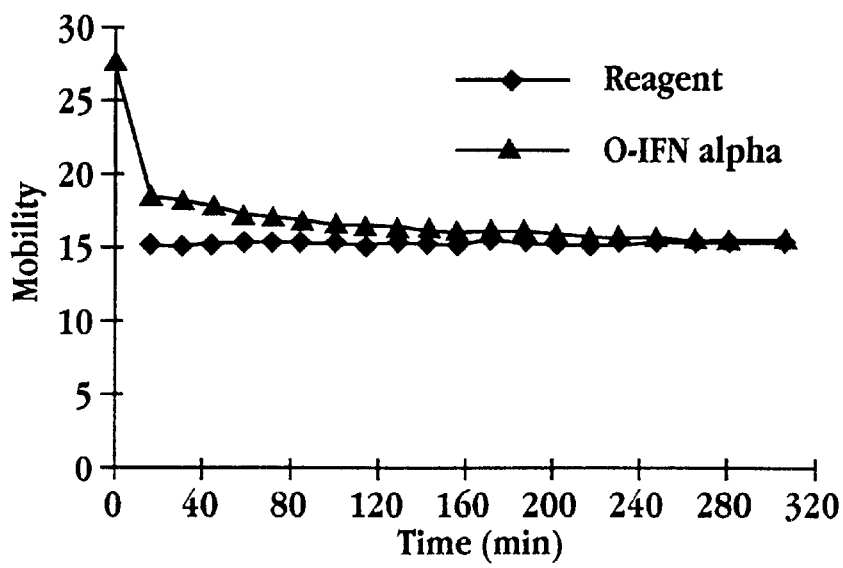

The degree of derivatization appears to be time dependent, as evidenced by the electropherogram in FIG. 4A. The trace in FIG. 4A was obtained by capillary electrophoresis and the methodology is set forth in the methods section below. The trace shows that after 2 and 18 minutes of reaction time with palmitic acid, the migration time of the palmitoylated interferon changed from 7 minutes to 7.8 minutes, respectively. Smaller changes in migration time up to 1 hour of incubation was observed. After 1 hour of reaction time, no further change in migration was observed.

The effect of protein:N-hydroxysuccinimide ester of palmitic acid ratio on palmitoylation was evaluated using capillary electrophoresis. As seen in FIG. 4B, at low ratios of protein:palmitic acid a more heterogeneous population of derivatized protein was formed, as evidenced by the broader peaks with lower mobility. At a ratio of 1:10 or higher a reproducible population of palmitoylated interferon α2b with an electrophoretic mobility of 9.5 minutes was obtained.

FIG. 5A is a plot which corresponds to the trace of FIG. 4B and shows the mobility of the interferon (α2b-palmitic acid conjugate as a function of protein:fatty acid ester (palmitic acid esterified with N-hydroxysuccinimide) ratio. The fatty acid ester has a mobility of about 23 and conjugation with interferon α2b at a 1:1 ratio decreasing the mobility to about 17. The mobility decreases slowly thereafter with increasing protein:fatty acid ester ratio.

FIG. 5B shows mobility as a function of time for the N-hydroxysuccinimide ester of oleic-acid (closed triangles) and for the oleic acid-interferon α2b conjugate prepared in a 50/50 v/v mixture of distilled water/DMSO and a protein:fatty acid ester ratio of 1:25 (closed diamonds). After about 30 minutes of incubation time, the mobility of the conjugate is about 17, with a slow continuous decrease in mobility with longer reaction time.

Further in support of the invention, interferon α2b and interferon α2a were derivatized as described above with fatty acids having between 12 and 24 carbon atoms. The conjugates prepared and the molar ratio of interferon α to the N-hydroxysuccinimide fatty acid ester are shown in Table 1. The mobility values shown in Table 1 were determined by capillary electrophoresis, as set forth in the methods section below.

TABLE 1

| Cytokine | Fatty Acid (No. Carbons) | Cytokine-Fatty Acid[1] Ratio | Mobility in SDS Gel[2] |
|---|---|---|---|
| Interferon α2b | Lauric Acid (C12) | 1:20 | nd[3] |
| Interferon α2b | Myristic Acid (C14) | 1:20 | nd |
| Interferon α2b | Palmitic Acid (C16) | 1:20 | nd |
| Interferon α2b | Stearic Acid (C18) | 1:20 | nd |
| Interferon α2b | Oleic Acid (C18, unsaturated) | 1:20 | nd |
| Interferon α2a | Lauric Acid (C12) | 1:25 | 12.532 |
| Interferon α2a | Myristic Acid (C14) | 1:25 | 12.533 |
| Interferon α2a | Palmitic Acid (C16) | 1:25 | 12.608 |
| Interferon α2a | Stearic Acid (C18) | 1:25 | 12.636 |
| Interferon α2a | Oleic Acid (C18, unsaturated) | 1:25 | 12.627 |
| Interferon α2a | Arachidic Acid (C20) | 1:25 | nd |
| Interferon α2a | Behenic Acid (C22) | 1:25 | nd |
| Interferon α2a | Lignoceric Acid (C24) | 1:25 | nd |
| Interferon α2a (control) | none | — | 13.085 |
| Interferon α2a in DMSO (control) | none | — | 13.213 |

[1]Ratio of cytokine to N-hydroxysuccinimide fatty acid ester.
[2]Determined by capillary electrophoresis.
[3]nd = not determined II. Characterization of the Conjugates The conjugates composed of interferon α and various fatty acids, prepared as described above, were characterized by electrophoresis (polyacrylamide gel electrophoresis (PAGE)) and were characterized for antiviral activity and receptor binding activity.

1. Gel Electrophoresis

Figure 6A:
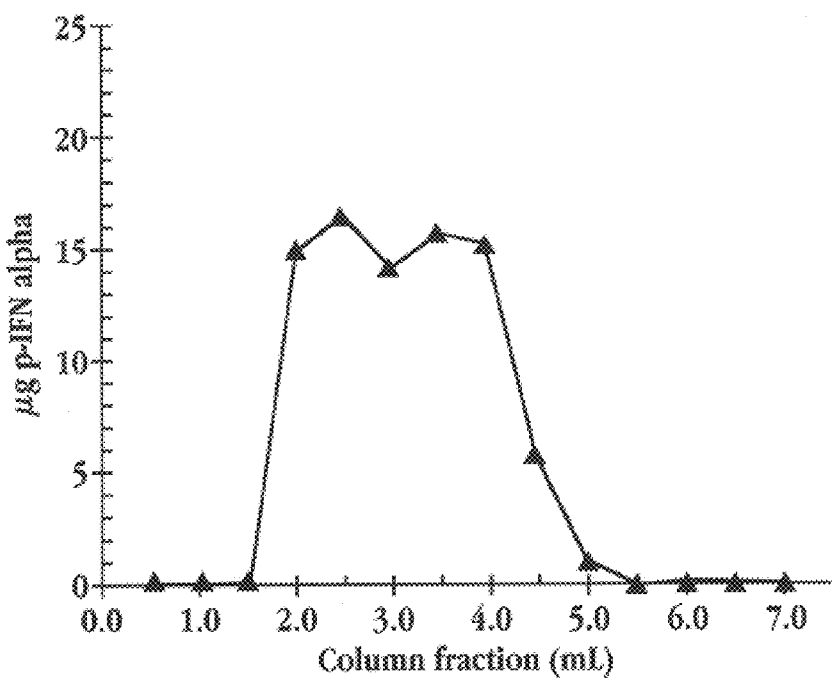

A chromatographic profile of interferon α2b acylated with palmitic acid on Sephadex G-25 column is shown in FIG. 6A. The intactness of the interferon α2b after lipid modification is evident and the individual column (Sephadex G25) fractions are shown in the SDS-PAGE pattern of FIG. 6B. Lane 1 in the profile is for a Bio-Rad molecular weight standard; lane 2 is for an interferon α2b standard and lanes 3–9 correspond to fractions taken at 1.5–5.5 ml from the Sephadex column (FIG. 6A).

Figure 6B:
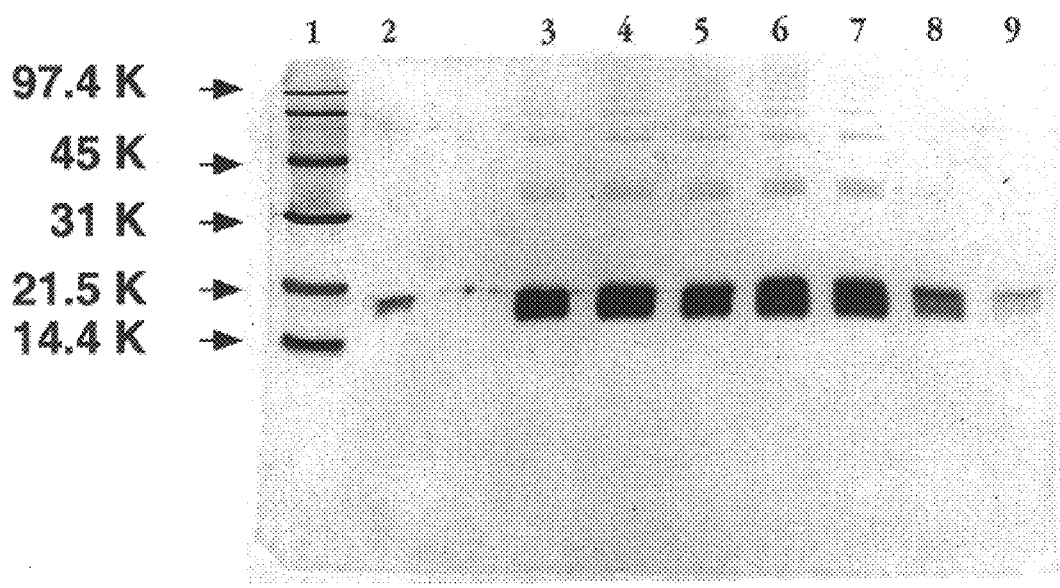
Figure 6C:
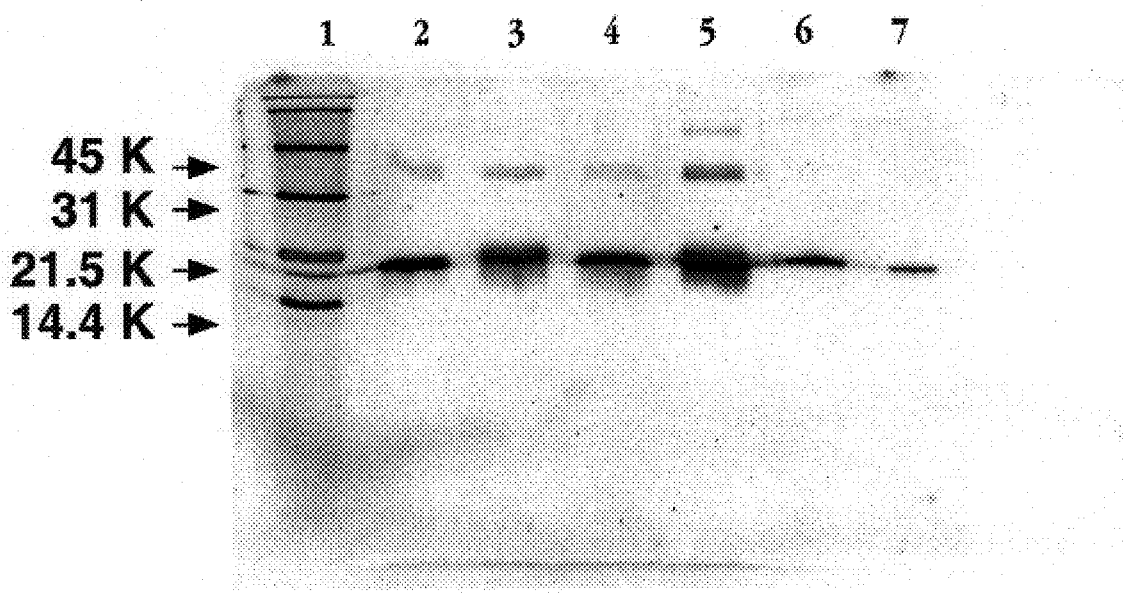

FIG. 6C is a SDS-PAGE profile comparing interferon α2b-palmitate conjugates prepared under various conditions. Lane 1 in the profile is a molecular weight standard; lane 2 is interferon α2b incubated in DMF; lane 3 corresponds to a conjugate of interferon α2b and palmitic acid prepared in DMF; lane 4 corresponds to interferon α2b incubated in DMSO; lane 5 corresponds to a conjugate of interferon α2b and palmitic acid prepared in DMSO; lane 6 is an interferon α2b standard, 100 ng; and lane 7 is an interferon α2b standard, 50 ng.

A comparison of the bands in lanes 3 and 5 shows that the yield of palmitoyl-interferon α2b prepared in DMSO was 15–20% higher than when the conjugate was prepared in DMF. Lanes 2 and 4 in FIG. 6C compare the effect of the two solvents, DMSO and DMF, respectively, on the protein alone. No differences in the bands are apparent, indicating that the neither solvent has a negative effect on the protein. The PAGE bands for the conjugate indicate a 6–10% increase in molecular weight of interferon α after acylation.

2. Antiviral Activity

The palmitate-interferon α2b conjugate prepared as described above was evaluated for antiviral activity to determine whether acylated cytokines in general retain biological activity. Antiviral activity was evaluated according the procedure described in Example 2, where the cytopathic effect inhibition assay using Georgia Bovine Kidney (GBK) cells and vesicular stomatitis virus (VSV) as the challenge virus. The results are shown in Table 2.

TABLE 2

| | Antiviral Activity (% of interferon-α2b) | |
|---|---|---|
| | conjugate prepared in DMSO[1] | conjugate prepared in DMF[1] |
| Interferon α2b[1] | 100% | 100% |
| palmitoyl-interferon α2b | 50% | 0% |

[1]Interferon α treated under the same conditions as the protein undergoing acylation.
[2]Palmitoyl-interferon α acylated in dimethylformamide (DMF) or in dimethylsulfoxide (DMSO).

The antiviral activity of interferon α2b was unaffected when the protein was treated to the conditions of the acylation reaction, except for addition of palmitic acid, in both dimethylformamide (DMF) and dimethylsulfoxide (DMSO). That is, 100% of the antiviral activity of interferon α was preserved. Acylation of the cytokine with palmitic acid in the solvent DMF resulted in a complete loss of activity. When the reaction was carried out in DMSO a 50% preservation of antiviral activity was achieved.

The loss in activity may be in part attributed to experimental conditions, and the assay was modified for greater control and accuracy. The GBK cells in 96-well microtiter plates were dosed with 50 μl interferon α2b reference solution of a conjugate sample. After incubation overnight the cells were infected with VSV virus. After incubation, washing, fixing and staining, the plates were read by a spectrophotometer to determine the antiviral activity of the compounds. The results, shown in Table 3, indicate enhanced activity of the novel derivatives compared to the parent protein.

TABLE 3

| Sample | Antiviral Activity |
|---|---|
| Interferon α2b (INF α2b) | 100% |
| Lauroyl-INF α2b | 210% |
| Myristol-INF α2b | 175% |
| stearoyl-INF α2b | 190% |
| oleyl-INF α2b | 200% |

In another experiment using the revised method, antiviral activity of interferon α2a derivatized with behenic and lignoceric acid was measured. The conjugate including behenic acid retained nearly 100% of the interferon α2a activity and the conjugate with lignoceric acid retained about 30% of interferon α2a antiviral activity.

Table 4 shows the antiviral activity of conjugates prepared with interferon γ.

TABLE 4

| Fatty Acid | Antiviral Activity (% of interferon γ) |
| --- | --- |
| Lauric Acid | 25% |
| Myristic Acid | 20% |
| Palmitic Acid | 22% |
| Stearic Acid | 40% |
| Oleic Acid | 10% |
| Arachidic Acid | 2% |
| Behenic Acid | 8% |
| Lignoceric Acid | 9% |

As noted above, the conjugates used in the studies reported herein were not separated or purified into single acyl-protein fractions. There may be an optimum degree of fatty acylation for maximum retention of biological activity of the cytokine—for example, a di-palmitoyl interferon α may have a higher, or lower, biological activity than tri-palmitoyl interferon α. Separation of the fractions for analysis can be readily performed by those of skill in the art to determine such an optimum, as evidenced by the work of Hashimoto, et al (*Pharm. Res.*, 6:171, 1989). Nonetheless, partial loss of antiviral activity does not exclude the possibility that other functions of interferon α are unchanged or perhaps increased. In fact, some cytokine functions do not involve receptor binding and can act directly on intercellular signaling pathways (Baron et al., *JAMA*, 266:1375, 1991). Also, partial loss of antiviral activity may be inconsequential or at least offset in view of the enhanced skin penetration, discussed below.

3. Receptor Binding

Binding of the conjugates composed of interferon α2a and behenic acid or lauric acid was determined in an assay using human keratinocytes, as described in Example 3. The results are shown in FIGS. 7A-7B, where FIG. 7A shows binding of iodinated interferon α2a to human keratinocytes as a function of concentration of interferon α2a. The binding of interferon α2a is concentration dependent and saturation of binding was not evident at 40 ng interferon α2a. Scatchard analysis indicated the dissociation constant was $5.1\times10^{-10}$M, with 1579 receptors per human keratinocyte cell (see insert in FIG. 7A).

FIG. 7B shows binding of conjugates of interferon α2a derivatized with behenic acid (closed circles) and lignoceric acid (closed circles) and, as a control, of interferon α2a treated with DMSO (closed squares) as a function of amount of interferon α2a. The behenic acid-interferon α2a conjugate had a binding comparable to that of the protein alone treated with DMSO.

4. Solubility

The relative hydrophobicity of the conjugates described above were determined by measuring the partition coefficient of each conjugate into stratum corneum. Powdered stratum corneum, prepared as described in Example 4, was incubated with radiolabeled interferon α2a and the lipid derivatized conjugates, prepared as described above, and the ratio of uptake (Kp) into the powdered stratum corneum to that remaining in the saline preparation was determined (Example 4). The results are shown in Table 5.

TABLE 5

| Conjugate | Kp |
|---|---|
| interferon α2a | 3.360 |
| lauric acid-interferon α2a | 4.404 |
| myristic acid-interferon α2a | 4.541 |
| palmitic acid-interferon α2a | 5.071 |
| stearic acid-interferon α2 | 4.508 |
| oleic acid-interferon α2a | 5.044 |
| arachidic acid-interferon α2a | 5.079 |
| behenic acid-interferon α2A | 3.555 |
| lignoceric acid-interferon α2a | 3.730 |
| DMSO treated interferon α2a | 3.906 |

The results show that the fatty acid derivatization of interferon increases the uptake relative to the parent protein, indicating an increase in hydrophobicity and greater affinity for the skin.

A similar study was conducted for interferon α2b and conjugates of interferon α2b, where the partition coefficient was determined in the conventional octanol/water system, at octanol/phosphate buffered saline ratios of 1:7 and 1:25. The results are shown in Table 6.

TABLE 6

| Test System | Conjugate | Kp | p value (paired t-test) |
|---|---|---|---|
| octanol/saline (1:7) | interferon α2b | 0.0348 | |
| | lauric acid-interferon α2b | 0.0737 | 0.103 |
| | myristic acid-interferon α2b | 0.0691 | 0.001 |
| | palmitic acid-interferon α2b | 0.0364 | 0.800 |
| | stearic acid-interferon αb | 0.0531 | 0.024 |
| | oleic acid-interferon α2b | 0.0329 | 0.540 |
| octanol/saline (1:25) | interferon α2b | 0.0373 | |
| | lauric acid-interferon α2b | 0.0434 | 0.423 |
| | myristic acid-interferon α2b | 0.0487 | 0.201 |
| | palmitic acid-interferon α2b | 0.0337 | 0.634 |
| | stearic acid-interferon αb | 0.0263 | 0.142 |
| | oleic acid-interferon α2b | 0.0475 | 0.265 |

5. Cutaneous Absorption

The rate and extent of skin penetration of the conjugates was determined in vitro according to the procedure described in Example 5. In these studies, interferon α2b and the palmitoyl derivative of interferon α2b were iodinated by the lactoperoxidase method set forth in Example 3. A preparation of each test compound was placed on full thickness human skin mounted in a diffusion cell and the downstream reservoir of the cell was monitored for 24 hours for amount of interferon α2b.

After 24 hours, the skin was removed from the test cells and the radioactivity associated with the skin was determined by gamma counting. These results are shown in Table 7 under the column headed "whole skin counts". The skin was then stripped ten times with Scotch™ tape and the radioactivity associated with each strip was determined separately. These values are reported in Table 7 in the column headed "stratum corneum". The skin after stripping was counted again to obtain the counts associated with the viable skin layers (epidermis, dermis and subcutaneous tissues), and this data is in the third column of Table 7. The skin stripping technique was validated by sectioning paraffin embedded stripped skin and viewing under a light microscope for complete removal of the stratum corneum.

TABLE 7

In vitro cutaneous absorption of interferon α2b and palmitoyl-interferon α2b into human breast skin

| Preparation | Whole Skin μg/cm², n = 6 | Stratum Corneum μg/cm², n = 6 | Viable Layers μg/cm², n = 6 |
|---|---|---|---|
| interferon α2b | 0.41 ± 0.11 (1.8% ± 0.5%) | 0.20 ± 0.08 | 0.23 ± 0.09 (0.98% ± 0.39%) |
| palmitoyl-interferon α2b | 2.11 ± 1.22 (11.5% ± 6.7%) | 0.23 ± 0.14 | 1.88 ± 1.16 (10.3% ± 6.4%) |

The results in Table 7 show that both the cutaneous and percutaneous absorption of the acylated cytokine was 5–6 fold greater than that of the cytokine alone. The amount of acylated interferon α2b and of interferon α2b in whole skin after 24 hours of treatment was 2.11±1.22 μg/cm² and 0.41±0.11 μg/cm², respectively. This represents 11.5±6.7% and 1.8%±0.5% of total drug applied, respectively. In the viable skin layers the difference in absorption between the derivatized protein and the parent protein was 8–10 fold, 1.88±1.16 μg/cm² (10.3%±6.4%) and 0.228±0.91 μg/cm² (0.98%±0.39%).

The calculated percutaneous absorption parameters for the preparations reported in Table 7 are shown in Table 8. Approximately two times higher flux was detected for the conjugate compared to the non-fatty acylated protein. The total amount of drug diffused in 24 hours was also about two times higher for the conjugate.

TABLE 8

In vitro percutaneous Absorption of interferon α2b and palmitoyl-interferon α2b through human breast skin

| Parameters | $^{125}$I-interferon α2b | $^{125}$I-palmitoyl-interferon α2b |
|---|---|---|
| Steady state flux (ng/cm²/h)[1] | 1.47 | 2.71 |
| Permeability coefficient (cm/h)[2] | $1.65 \times 10^{-5}$ | $3.03 \times 10^{-5}$ |
| Diffusion coefficient (cm²/sec)[3] | $6.85 \times 10^{-12}$ | $5.45 \times 10^{-12}$ |
| Total amount diffused in 24 h: (ng/cm²) | 23.8 ± 17.4 | 42.7 ± 25.70 |

[1]Determined by regression analysis of the linear portion of cumulative amount of drug diffused (Q) vs. time (t) curve.
[2]Permeability coefficient (P) was calculated from Fick's first law: $(dQ/dt)^{ss} = J^{ss} = P\Delta C$; where $P = Kp\ D/h$ [$J^{ss}$ = steady state flux; ΔC = concentration difference between donor and receiver compartments; Kp = partition coefficient between skin and the preparation]
[3]Diffusion coefficient was calculated from $D = h^2/6L$; where h = thickness of the stratum corneum (0.001 cm); L = lagtime (sec).

Figure 8A:
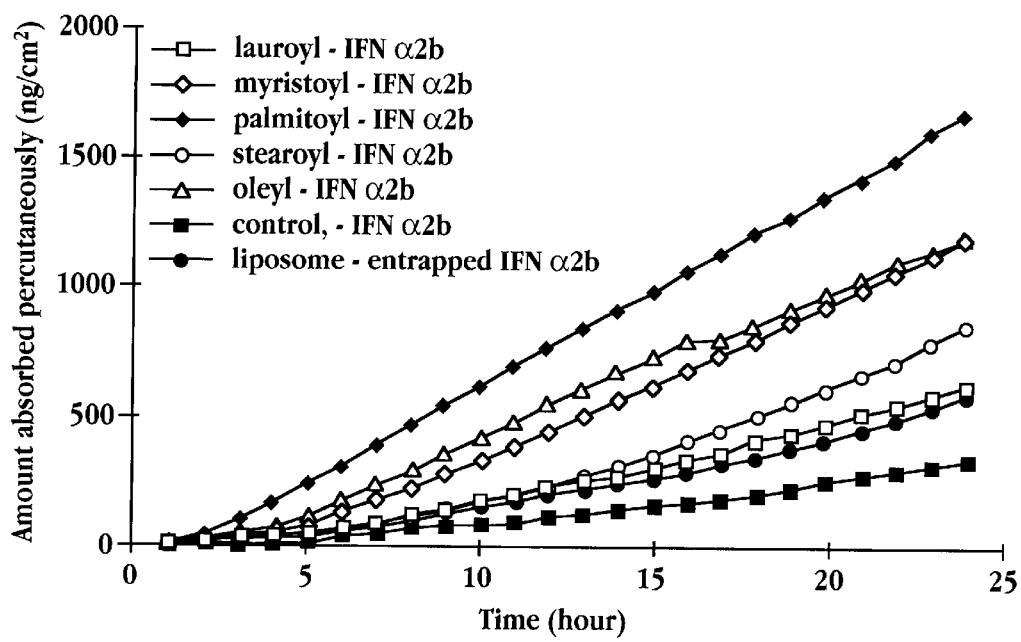
Figure 8B:
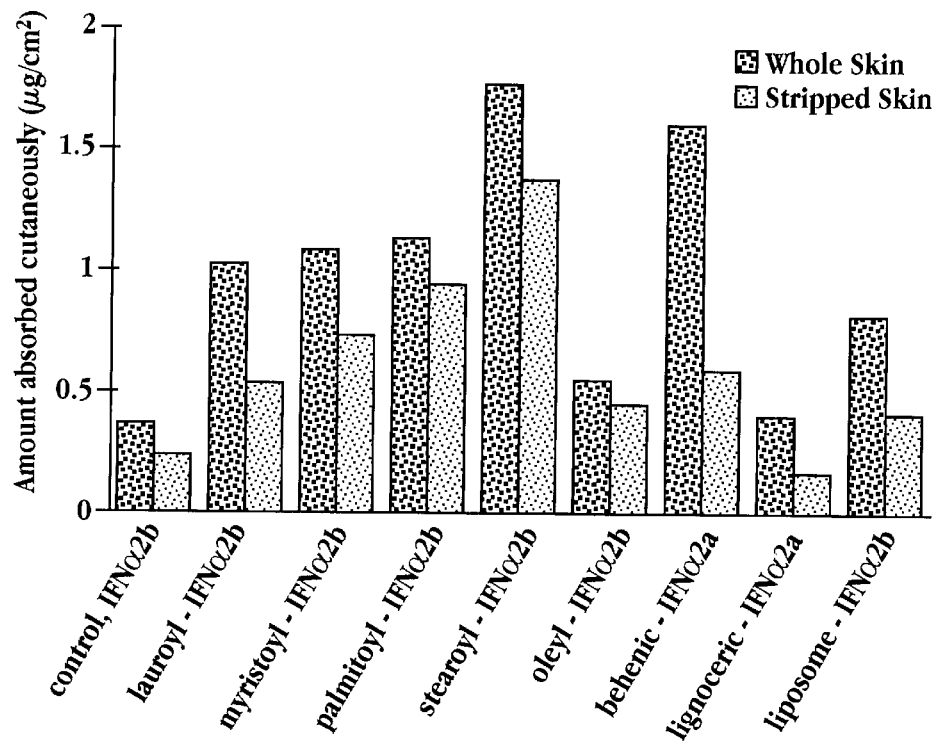

The cutaneous and percutaneous absorption into and through skin was also measured in vitro for conjugates of interferon α2b and lauric acid, myristic acid, palmitic acid, stearic acid and oleic acid, prepared as described above. A preparation of liposomes having entrapped interferon α2b was also tested. The results are shown in FIGS. 8A-8B, where in FIG. 8A the amount of interferon α2b absorbed percutaneously is reported, e.g., the quantity of interferon α2b in the downstream receiving volume after 24 hours. FIG. 8B shows the amount of interferon α2b in the skin after 24 hours.

The figures show that fatty acylation of the cytokine enhanced percutaneous absorption significantly when compared to liposomally-entrapped interferon α2b (closed circles) and interferon α2b alone (closed squares). As seen in FIG. 8A, the conjugate with palmitic acid (closed triangles) had the highest percutaneous absorption, followed by oleic acid (open triangles), myristic acid (open diamonds), stearic acid (open circles) and lauric acid (open squares). Interferon α2b entrapped in liposomes (closed squares) and the control formulation of interferon α2b alone (closed squares) had the lowest cutaneous penetration rates.

FIG. 8B is a bar graph showing the amount of interferon α in whole skin and in the viable skin, that is, skin after removal by tape stripping of the stratum corneum for the formulations with interferon α2b shown in FIG. 8A and for two formulations with interferon α2a; behenic acid-interferon α2a and lignoceric acid-interferon α2a.

The in vitro skin penetration results show that fatty acylation of a cytokine is effective to significantly increase the skin penetration of the cytokine. "Significantly is increase" or "substantially higher rate of skin penetration" as used herein means that the skin penetration, that is cutaneous or transcutaneous penetration, is increased by at least two-fold, more preferably three-fold, over the skin penetration of the cytokine alone.

III. Method of Use

In another aspect, the invention includes a method of transdermally delivering a cytokine by preparing a conjugate of the cytokine as described above and applying the conjugate to the skin. In a preferred embodiment of this aspect, the conjugate is composed of interferon α and a fatty acid having between 12–24 carbon atoms and is administered topically for treatment of genital warts caused by human papilloma virus.

The conjugate is typically applied to the skin in a pharmaceutically acceptable preparation, by which is meant any preparation or device suitable for maintaining the conjugate in contact with the skin. For example, such a preparation can be a simple saline solution containing the conjugate that is gelled with a suitable gelling agent, such as a cellulose derivative, to a viscosity suitable for application. In general, topical gels, creams or ointments are preferred, however non-rate limiting transdermal devices that can incorporate the conjugate are also suitable.

Preferred cytokines for use in the invention are interferons and interleukins. The interferons are a group of immunoregulatory proteins synthesized by T lymphocytes, fibroblasts and other types of cells following stimulation with viruses, antigens, mitogens, double-stranded DNA or lectins. Interferons have immunomodulatory functions and enhance the ability of macrophages to destroy tumor cells, viruses and bacteria. Interferons are classified as α and β, which have antiviral properties, and as γ which is known as immune interferon. The α and β interferons share a common receptor, and γ interferon has its own receptor. Interferons α and β are synthesized mainly by leukocytes and fibroblasts and are acid stable. Interferon γ is acid labile and is formed mainly by T lymphocytes stimulated by antigen or mitogen, but is also secreted by natural killer cells.

The ability of interferons to prevent infection of noninfected cells is species specific, it is not virus specific. Essentially all viruses are subject to the inhibitory action of interferons. Interferons induce formation of a second inhibitory protein that prevents viral messenger RNA translations.

Interferon α2b (recombinant) is a 18.4 kDa molecular weight polypeptide consisting of 165 amino acids. Interferon α shows multiple biological effects including antiviral, antiproliferative and immunomodulatory. The mechanism of action is through binding to specific cell surface receptors. The binding induces protein kinase and 2'5'-oligoadenylate synthetase (Clemens, Br. *J. Clin. Pract.,* 42:5, 1988). These enzymes can inhibit protein synthesis in the cell and therefore can prevent a virus from replicating (Pestka, et al., *Ann. Rev. Biochem.,* 56:727, 1987).

IV. EXAMPLES

The following examples illustrate methods of preparing, characterizing, and using the acylated cytokine conjugate of the present invention. The examples are in no way intended to limit the scope of the invention.

A. Materials

Interferon α2b was provided by Schering-Plough Research Corporation, Kenilworth, N.J. Interferon α2a and interferon γ were obtained from (Roche Biosciences). The fatty acids lauric acid, myristic acid, palmitic acid, stearic acid, arachidic acid, lignoceric acid, oleic acid and behenic acid were obtained from Sigma Chemical Co. (St. Louis, Mo.). N-hydroxysuccinimide was obtained from Sigma Chemical Co.

B. Methods

1. Page

Polyacrylamide gel electrophoresis (PAGE) in the presence of sodium dodecyl sulfate (SDS) was carried out in a Mini-Protean II (BioRad, Missisauga, Ontario, Canada) apparatus according to Laemmli (*Nature*, 227:680, 1970). The gel consisted of a running gel containing 14% (w/v) acrylamide and a stacking gel containing 5-acrylamide. The gel thickness was 1.0 mm. The electrophoresis buffer was 25 mM Tris, 192 mM glycine, 0.01% (w/v) SDS, pH 8.6. Electrophoresis was carried out at 200 V constant voltage. The electrophoresis was conducted for 45 minutes. After electrophoresis, the gels were silver stained to detect the protein (Foldvari, et al., *Biochem Cell Biol.*, 68:499, 1990).

2. Capillary Electrophoresis

Capillary electrophoresis studies were performed using a P/ACE System 5500 (Beckman Instruments, Fullerton, Calif.) with diode array detector and System Gold Software. Free-zone electrophoresis was carried out using an uncoated capillary (57 cm×75 μm) at 23° C. and 20 KV with a 5 second pressure injection. The running buffer was 0.6% w/v sodium borate ($Na_2B_4O_7.10H_2O$) and 0.5% boric acid, pH 8.75. The detector was used at 200–300 nm. Prior to use, the capillary was washed with NaOH (0.1M) for 10 minutes and for 1 minute between each run.

Example 1

Preparation of Palmitoyl Derivative of Interferon α2b

Palmitoyl derivatives of interferon α2b were synthesized according to the scheme shown in FIG. 2, where the N-hydroxysuccinimide ester of palmitic acid (NHS-P) was synthesized as follows. Equal molar amounts of palmitic acid and N-hydroxysuccinimide were mixed together in ethyl acetate followed by addition of dicyclohexylcarbodimide (DCI). The mixture was stirred overnight at 4° C. Dicyclohexylurea was filtered out and NHS-P was recrystallized from the filtrate by the addition of ethanol at 4° C. $^1$H-NMR studies on NHS-P confirmed the expected structure (results not shown).

The palmitoyl derivative of interferon α2b was prepared follows. NHS-P was dissolved in DMF or DMSO and added at 25:1 molar ratio to the PBS buffer (7.5 mM $Na_2HPO_4$, 2.5 mM $NaH_2PO_4$, 151.2 mM NaCl) containing interferon α2β at pH 7.2. The mixture was kept at room temperature for 3 hours with occasional gentle agitation. After the reaction, DMF or DMSO was removed under vacuum and the residue was redissolved in sterile distilled water.

The palmitoyl-interferon α2b derivative was separated from free fatty acid by chromatography on Sephadex G-25 column (Pharmacia, Uppsala, Sweden). The yield of palmitoyl-interferon α2b was dependent on the starting concentration, where a 25 μg batch and a 100 μg batch yielded 50.2% and 84.0%, respectively, as determined by the densitometry of the palmitoyl-interferon bands of the column fractions. Fractions containing protein were pooled, freeze-dried and reconstituted with sterile distilled water before use.

A portion of each fraction was used for polyacrylamide gel electrophoresis (PAGE) and silver staining according to the procedure described above in the Methods section, and SDS-PAGE profiles of palmitoyl-interferon α2b are shown in FIGS. 6A–6B.

Example 2

Antiviral Activity of the Conjugate

Antiviral activity of palmitoyl derivatives of interferon α was determined by the cytopathic effect inhibition assay using Georgia Bovine Kidney (GBK) cells, which are sensitive to human interferon α, and vesicular stomatitis virus (VSV) as the challenge virus (Ohmann, et al., *J. Gen. Virol.*, 65:1485, 1984). The reference standard was interferon α2b, specific activity 2.24×10$^8$ IU/mg. The results are shown in Table 2.

Example 3

Conjugate Receptor Binding

A. Iodination of Interferon

Iodination of interferon α and conjugates of interferon was carried out using the lactoperoxidase method (Sarkar, et al., *Methods Enzymol.*, 119:263, 1986). Briefly, 2 mCi $^{125}$I, obtained from Amersham Corporation (Oakville, Ontario, Canada), was neutralized by adding 3 volumes of 0.03 N HCl and the total was made up to 25 μl with 0.2 M sodium phosphate buffer pH 7.2. The following were added to the mixture: 50 μl Enzymobeads (Bio-Rad), 15 μl freshly made 2% β-D-glucose in 0.1 M sodium phosphate buffer, pH 7.2, 10 μl interferon (approximately 10 μg protein) The reaction mixture was incubated for 20 minutes at room temperature. The reaction was stopped by adding 25 μl of 1 M sodium azide and incubating for 15 minutes. Finally, 125 μl of saturated L-tyrosine in PBS was added and the mixture transferred onto a Sephadex G25 column. Fractions containing the protein were pooled.

In another method, the iodination mixture was transferred onto Bio-Spin columns (exclusion limit 6,000) (Bio-Rad) and iodinated protein recovered by a brief low speed centrifugation. To remove any possible residue of unbound iodine the protein preparation was dialyzed overnight against 1 mM sodium iodide in PBS. This procedure removed practically all acid soluble iodine as determined by trichloroacetic acid precipitation.

The final preparations of $^{125}$I-interferon α2A and $^{125}$I-palmitoyl-interferon α had specific activities of 2.05×10$^7$ cpm/μg and 1.94×10$^7$ cpm/μg protein, respectively. The iodinated interferon α and palmitoyl-interferon α were examined by PAGE for intactness, and the protein concentration was determined by densitometry.

B. Receptor Binding

Figure 7A:
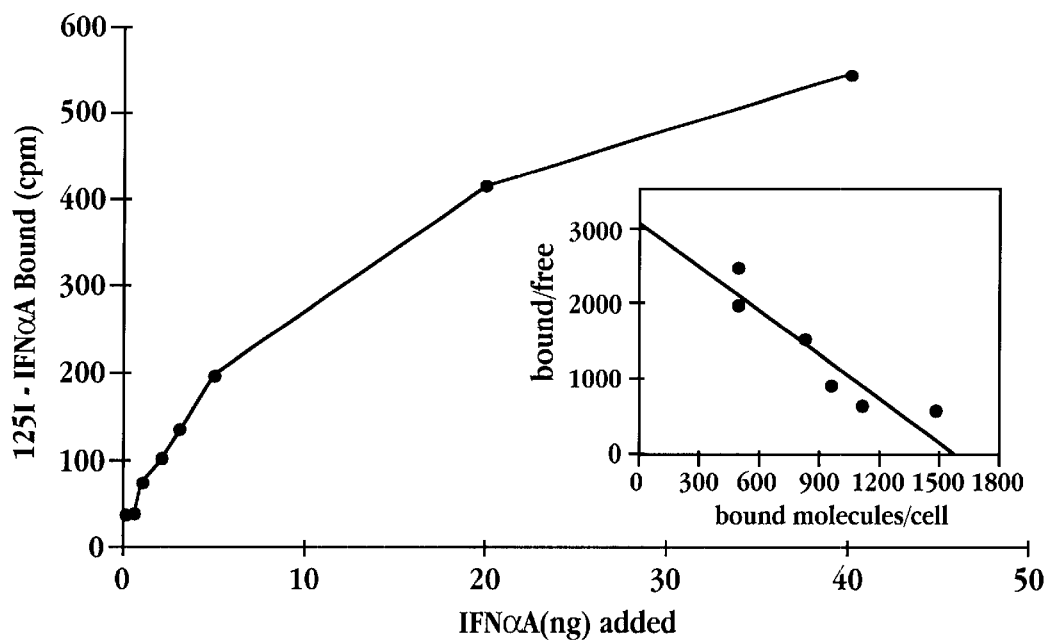
Figure 7B:
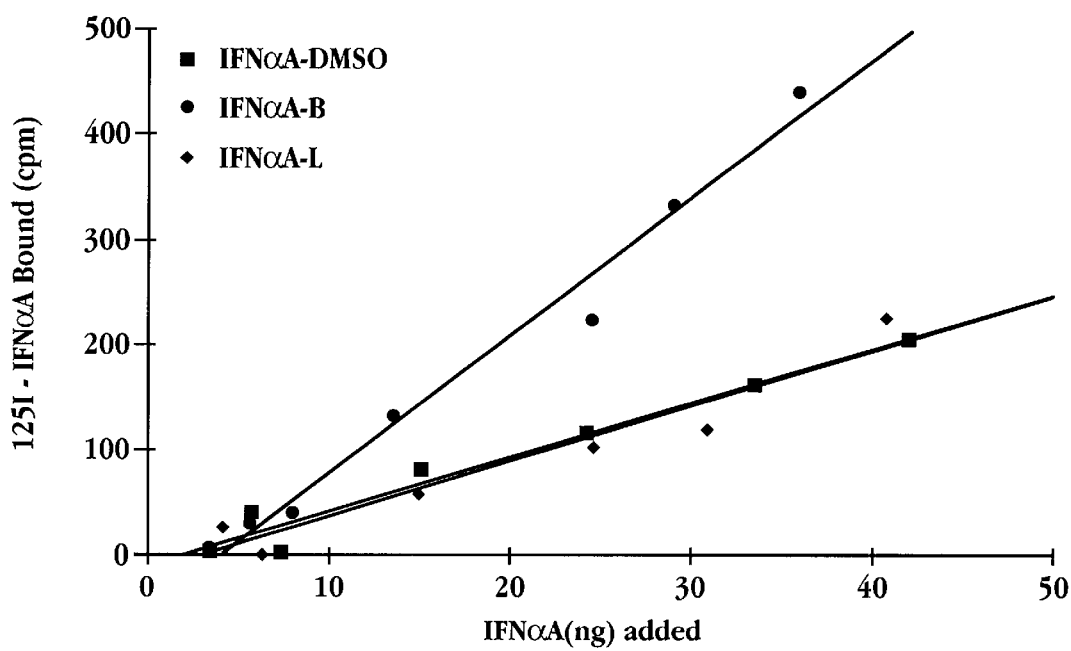

A single cell suspension of human keratinocyte cells (isolated from patients undergoing mammoplasty within one day of surgery) from a confluent culture was prepared and resuspended at 2×10$^6$ cells/mL in KSF-medium. Two mL of KSF-medium was added to each well of a 6-well flat bottom tissue culture plate and incubated at 37° C. until the cells in each well reached confluency. $^{126}$I-interferon α2a conjugates, prepared as described above, at concentrations between 0.5–40 ng and incubated at 4° C. for 5 hours on a shaker. The medium was aspirated from each well to gamma counting tubes and washed three times with 1 mL of cold HBSS. The $^{125}$I-interferon sample wells were scraped using cell scrapers and examined using an inverted microscope. The cell suspension was transferred to the gamma counting tubes and the wells were washed three time with 0.5 mL of HBSS and transferred to the same tubes. One mL of HBSS was added to every well to wash the wells and the HBSS was transferred to another tube. The radiation of each tube was counted using a gamma counter. The cells in the cell control well were detached using 0.25% trypsin. The cells were counted and evaluated to detect viability by trypan blue exclusion. The results are shown in FIGS. 7A–7B.

Example 4

Measurement of Partition Coefficients

Human skin was cut into 1×1 cm squares and placed into 60° C. water for 1 minute. The epidermis was separated with forceps. The peeled skin pieces were placed epidermis side down on filter paper saturated with 1% trypsin solution and incubated at room temperature for 1 hour. Then the digested epidermis was washed with water. The stratum corneum pieces were blot dried with tissue and further dried in a freeze dryer overnight. The stratum corneum pieces were ground to form powder using liquid nitrogen. The portion that can pass through a 60-mesh but not 80-mesh sieve was collected for partition coefficient determination.

Five milligrams of powdered stratum corneum was weighed into each vial. Fifty μl of fatty acid derivatized $^{125}$I-interferon α in phosphate buffered saline was added to cover the stratum corneum. Empty vials without powdered stratum corneum were used as controls. The mixture was incubated for 24 hours at 32° C. with gently shaking followed by centrifugation at 14,000 rpm for 5 seconds. The supernatant was counted by gamma counting. The powder was washed three times by adding 50 μl phosphate buffered saline. After washing, the stratum corneum powder left in the vial was counted.

The partition coefficient (Kp) was calculated as the ratio of ($cpm_{psc}$/weight of psc)/($cpm_{PBS}$/volume of PBS) (psc= powdered stratum corneum; PBS=phosphate buffered saline). The values are shown in Table 5.

Example 5

In Vitro Cutaneous and Percutaneous Absorption

The rate of diffusion of palmitoyl-interferon α2b across full thickness human breast skin (freshly obtained from plastic surgery and kept at −20° C. until used within 1 week) was investigated using Teflon®, Flow-Thru Diffusion Cells (Crown Glass Co. Inc., Somerville, N.J.) (Bronaugh and Stewart, *J. Pharm. Sci.*, 74:64 1985), which have a surface area for diffusion of 0.32 cm$^2$. The diffusion cells were operated with a continuous perfusion fluid flow of PBS pH of 7.2 on the downstream side in order to maintain sink conditions. The flow rate of the perfusion fluid was 3 mL per hour.

The diffusion cells were mounted in a diffusion cell heater (Crown Glass Co. Inc.) to maintain the temperature at 37° C. with circulating water. Each cell was connected to a fraction collector and each experiment was conducted for a continuous period of 24 hours over which time samples were collected at intervals.

The test preparations consisted of 0.1 mL solution [PBS buffer] or 0.1 g methylcellulose 1500 cP [2.5%] gel hydrated with PBS labeled with $^{125}$I-palmitoyl-interferon α2b. The test preparations were instilled into the cells at concentration of 20×10$^6$ IU (89.3 μg) of palmitoyl-interferon α2b per g or mL product. The average amount of interferon applied was 20.7 μg/cm$^2$ skin surface area. The quantity of palmitoyl-interferon α2b in the collected fractions was determined by gamma counting and the results are shown in Table 7.

After 24 hours, the skin was removed from the diffusion cell and rinsed thoroughly with cold (4° C.) PBS (3×15 mL) and the skin was blotted with tissue paper. The skin surface was swabbed with a cotton tip applicator dipped into PBS containing 0.5% Tween 80 two times to remove surface-bound drug. Care was taken not to disturb the stratum corneum. The skin was carefully folded (epidermal sides together) to avoid contamination of dermal side and placed into glass tubes. The radioactivity associated with the skin was determined by gamma counting and was considered to be the "whole skin" counts. The skin was then stripped ten times with a Scotch tape and the radioactivity associated with each strip was determined separately. The skin after the stripping was counted again in a clean tube to obtain the counts associated with the viable skin (epidermis, dermis and subcutaneous tissue). The skin stripping technique was validated by sectioning the paraffin embedded stripped skin to observe the complete removal of the stratum corneum in the light microscope (results not shown).

Trichloroacetic acid (TCA) precipitation was used to determine free and bound iodine label in percutaneous fractions and skin homogenate prepared from treated skin samples. TCA was added to each sample to 5% w/v concentration and was incubated at 4° C. overnight. The supernatants and pellets were analyzed by gamma counting after centrifugation in a Beckman Microfuge at 14,000 rpm for 15 minutes. The experiments with TCA precipitation from skin homogenates (after tape stripping) and fractions showed that 40–50% of radioactivity was precipitated from both interferon α2b and palmitoyl-interferon α2b, indicating that protein, not just the free iodine label, was present. The results are shown in Table 7.

Although the invention has been described with respect to particular embodiments, it will be apparent to those skilled in the art that various changes and modifications can be made without departing from the invention.

It is claimed:

1. A pharmaceutical composition for dermal or transdermal administration of a cytokine, comprising a conjugate composed of a cytokine and at least one unsaturated fatty acid moiety having between 16 –20 carbon atoms covalently attached to the cytokine, said conjugate having a substantially higher rate if skin penetration than the cytokine alone.

2. The composition of claim 1, wherein said cytokine is selected from the group consisting of interferons and interleukins.

3. The composition of claim 1, wherein said cytokine is selected from the group consisting of interferon α, interferon β, interferon γ, interleukin 1, interleukin 4 and interleukin 12.

4. The composition of claim 1, wherein said fatty acid is oleic acid.

5. The composition of claim 1, wherein said cytokine is an interfon α.

* * * * *

SEQUENCE LISTING

<160> NUMBER OF SEQ ID NOS: 1

<210> SEQ ID NO 1
<211> LENGTH: 165
<212> TYPE: PRT

-continued

```
<213> ORGANISM: Homo sapiens

<400> SEQUENCE: 1

Cys Asp Leu Pro Gln Thr His Ser Leu Gly Ser Arg Arg Thr Leu Met
 1               5                  10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Asp Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```